US00PP11361P

United States Patent [19]

Salmon

[11] Patent Number: Plant 11,361

[45] Date of Patent: Apr. 25, 2000

[54] BRACHYCOME PLANT NAMED 'HAPPY FACE PINK'

[75] Inventor: Alexander David Salmon, Gapsted, Australia

[73] Assignee: Outback Plants Pty. Ltd., The Patch, Australia

[21] Appl. No.: 09/177,288

[22] Filed: Oct. 22, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Kent L. Bell
*Attorney, Agent, or Firm*—C. A. Whealy

[57] ABSTRACT

A new and distinct cultivar of Brachycome plant named 'Happy Face Pink', characterized by its compact and spreading growth habit; freely branching plant habit; numerous large inflorescences with dark pink ray florets; and erect peduncles that hold inflorescences above the foliage.

2 Drawing Sheets

BACKGROUND OF THE INVENTION

The present invention relates to a new and distinct cultivar of Brachycome plant, botanically known as *Brachycome formosa*×*Brachycome segmentosa* Hybrid and referred to by the cultivar name 'Happy Face Pink'. The new Brachycome is marketed under the trade name Jumbo Mauve.

The new Brachycome is a product of a planned breeding program conducted by the Inventor in Park Orchards, Victoria, Australia. The objective of the program is to create new compact Brachycome cultivars with large inflorescences that are suitable for a range of climatic conditions.

The new Brachycome originated from a cross by the Inventor of the nonpatented *Brachycome formosa* cultivar 'Pilliga Posy', as the female, or seed, parent with an unidentified selection of *Brachycome segmentosa* Hybrid as the male, or pollen, parent. The cultivar 'Happy Face Pink' was discovered and selected by the Inventor as a flowering plant within the progeny of the stated cross in a controlled environment in Park Orchards, Victoria, Australia.

Asexual reproduction of the new Brachycome by terminal cuttings taken in a controlled environment in Park Orchards, Victoria, Australia, has shown that the unique features of this new Brachycome are stable and are reproduced true to type in successive generations.

SUMMARY OF THE INVENTION

The new Brachycome has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Happy Face Pink' and distinguish 'Happy Face Pink' as a new and distinct cultivar:

1. Compact and spreading growth habit.
2. Freely branching plant habit.
3. Numerous large inflorescencs with dark pink ray florets.
4. Erect peduncles that hold inflorescences above the foliage.

Compared to plants of the female parent, the cultivar 'Pilliga Posy', plants of the new Brachycome have darker green leaves with more deeply lobed margins and longer stems. Additionally plants of the cultivars 'Pilliga Posy' and 'Happy Face Pink' differ in ray floret color.

Compared to plants of the male parent, the unidentified selection of *Brachycome segmentosa* Hybrid, plants of the new Brachycome are more compact and have broader leaf lobes. Additionally plants of the unidentified selection of *Brachycome segmentosa* Hybrid and 'Happy Face Pink' differ in ray floret color.

BRIEF DESCRIPTION OF THE PHOTOGRAPHS

The accompanying colored photographs illustrate the overall appearance of the new Brachycome, showing the colors as true as it is reasonably possible to obtain in colored reproductions of this type.

The photograph on the first sheet comprises a top perspective view of a typical potted plant of 'Happy Face Pink'.

The photograph on the second sheet comprises a close-up view of typical inflorescences of 'Happy Face Pink'. Floret and foliage colors in the photographs may appear different from the actual colors due to light reflectance.

DETAILED BOTANICAL DESCRIPTION

The following observations, measurements, values, and comparisons describe plants grown in Victoria, Australia, under outdoor conditions with day temperatures ranging from 12 to 40° C., night temperatures ranging from 6 to 25° C., and light levels ranging from 5,000 to 9,000 footcandles. Color references are made to The Royal Horticultural Society Colour Chart except where general terms of ordinary dictionary significance are used.

Botanical Classification: *Brachycome formosa*×*Brachycome segmentosa* Hybrid cultivar 'Happy Face Pink'.

Parentage:

*Male or pollen parent.*—Unidentified selection of *Brachycome segmentosa* Hybrid.

*Female or seed parent.*—*Brachycome formosa* cultivar 'Pilliga Posy', not patented.

Propagation:

*Type.*—By cuttings.

*Time to initiate and develop roots.*—Summer: About 10 to 20 days at temperatures of 25° C. Winter: About 15 to 30 days at temperatures of 20° C.

*Roofing habit.*—Fine, fibrous and freely branching.

Plant description:

*General appearance.*—Compact, upright and spreading, flat to somewhat rounded herbaceous plant with erect peduncles. Suitable for 15-cm containers and hanging baskets. To produce a 15-cm finished flowering plant from rooted cuttings, 10 to 14 weeks are required depending on temperature and light level.

*Plant height.*—About 10 to 25 cm from soil level to top of inflorescences.

*Plant diameter or spread.*—About 25 to 40 cm.

*Branching.*—Freely branching, numerous lateral branches develop after removal (pinching) of the terminal apex.

*Growth rate/vigor.*—Moderate.

*Stem description.*—Lateral branch length: About 2.5 to 12.5 cm. Lateral branch diameter: About 1.5 to 2.5 mm. Internode length: About 0.3 to 2.2 cm. Texture: Young, slightly pubescent; older, glabrous. Color: 146D to 183A.

*Foliage description.*—Arrangement: Alternate, single. Quantity: About 9 to 31 per lateral branch. Shape: Broadly spatulate in outline with lobed and toothed margins. Apex: Broadly lobed with each segment usually having 2 to 3 teeth. Base: Sessile, somewhat clasping. Length: About 1.6 to 4.8 cm. Width: About 0.7 to 2.8 cm. Margins: 5 to 9-lobed with zero to three small teeth. Texture: Smooth, slightly leathery; glabrous surfaces, sparse short hairs on margins. Color: Young leaves, upper surface: 137C. Young leaves, lower surface: 137C. Fully expanded leaves, upper surface: 137B to 137C; venation, 146 to 146D. Fully expanded leaves, lower surface: 137B to 137C; venation, 146C to 146D.

Flowering description:

*Inflorescence.*—Single daisy-type composite inflorescence form. Florets arranged acropetally on a capitulum. Inflorescences last on the plant for about 6 to 12 days and about 7 to 10 days as a fresh cut flower. Self-cleaning.

*Natural flowering season.*—Natural flowering season is spring to fall; flowering continuous during this period.

*Response time.*—About 5 to 10 weeks.

*Quantity of inflorescences.*—About one to four per lateral branch with numerous inflorescences per plant.

*Inflorescence diameter.*—About 3.3 to 4.6 cm.

*Inflorescence depth (height).*—About 1.4 cm.

*Disc diameter.*—About 1.2 to 1.4 cm.

*Inflorescence aspect.*—Flat with ray florets becoming somewhat reflexed at maturity.

*Rate of inforescence opening.*—About 6 to 12 days.

*Fragrance.*—Very faint, honey-like.

*Inflorescence buds.*—Shape: Spherical. Length: About 7 mm. Diameter: About 6 to 7 mm. Color: 157C.

*Ray florets.*—Quantity: About 29 to 38 florets per inflorescence arranged in one to two rows. Shape: Narrowly oblanceolate. Apex: Blunt, rounded. Base: Attenuate. Margin: Entire. Aspect: Flat. Length: About 1.4 to 1.9 cm. Width: About 2 to 3 mm. Texture: Smooth, glabrous, thin. Color: When opening, upper surface: 69A. When opening, lower surface: 73D. Mature, upper surface: 80B, with further development, floret color fades to 78D. Mature, lower surface: 80C.

*Disc florets.*—Shape: Tubular with five lobes. Length: About 4 mm. Width: About 1 mm. Texture: Sparse glandular hairs. Color: Immature: 153A. Mature: 153A; tube, 153D. Number of disc florets per inflorescence: Numerous.

*Peduncle.*—Length: About 5.6 to 5.9 cm. Strength: Initially somewhat flexible becoming fairly rigid; erect or sometimes curved upwards. Texture: Smooth, glabrous. Color: 138B with 187A apex.

*Involucral bracts.*—Arrangement: Imbricate. Quantity: About 14 to 23 per inflorescence. Shape: Broadly oblong. Apex: Fringed. Margin: Entire to faintly fringed. Texture: Somewhat fleshy. Color: 138B.

*Androecium.*—Only present on disc florets. Stamen number: Five per disc floret. Anther shape: Oblong to linear. Anther color: 163D. Amount of pollen: Moderate. Pollen color: 15C.

*Gynoecium.*—Pistil number: One per floret. Stigma shape: Bilobate. Style length: About 3 mm. Style color: 154A. Stigma color: 154A.

Disease resistance: May be susceptible to Botrytis and fungal leaf spot diseases.

Seed production: Seed production has not been observed.

It is claimed:

1. A new and distinct cultivar of Brachycome plant named 'Happy Face Pink', as illustrated and described.

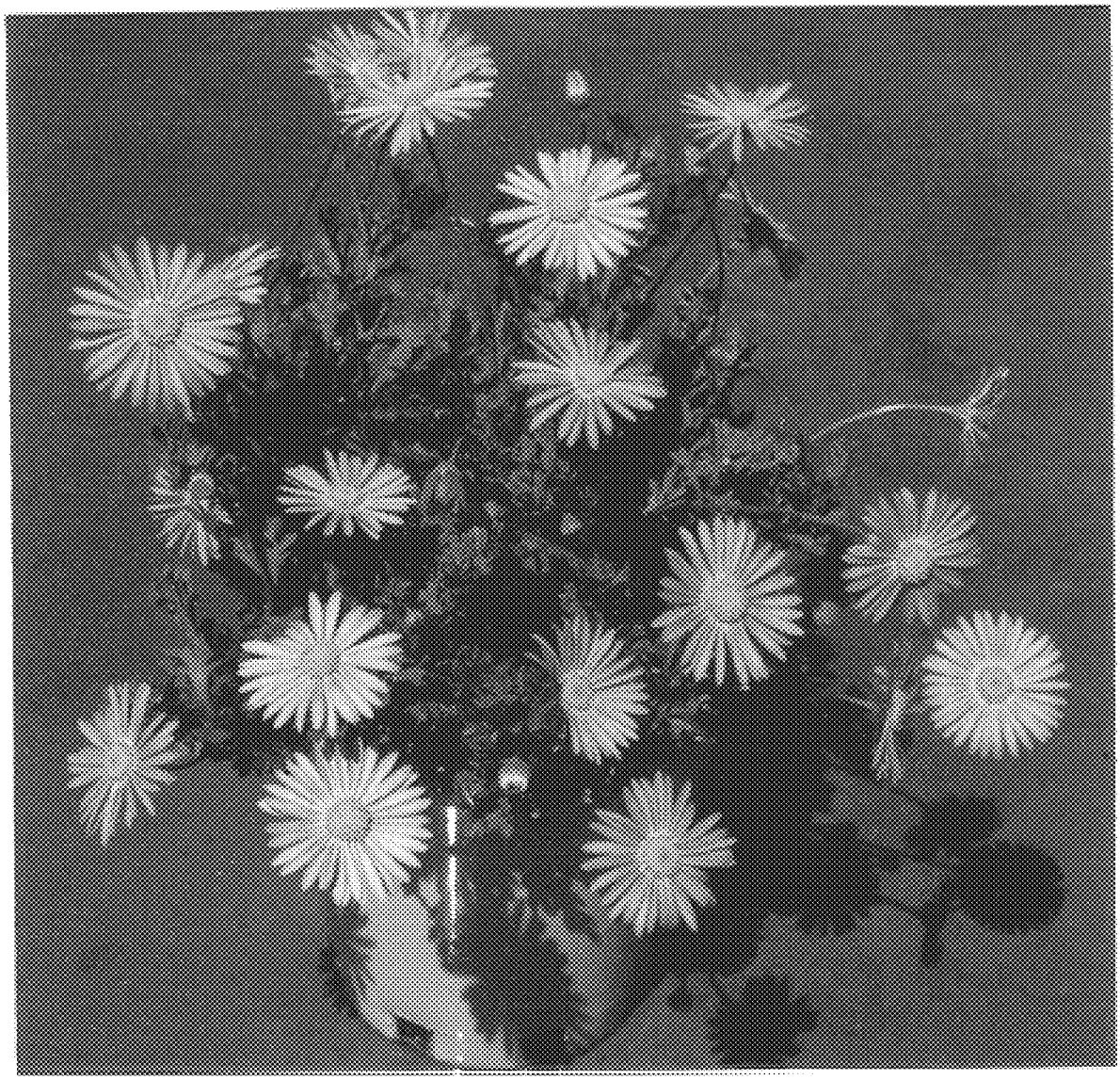

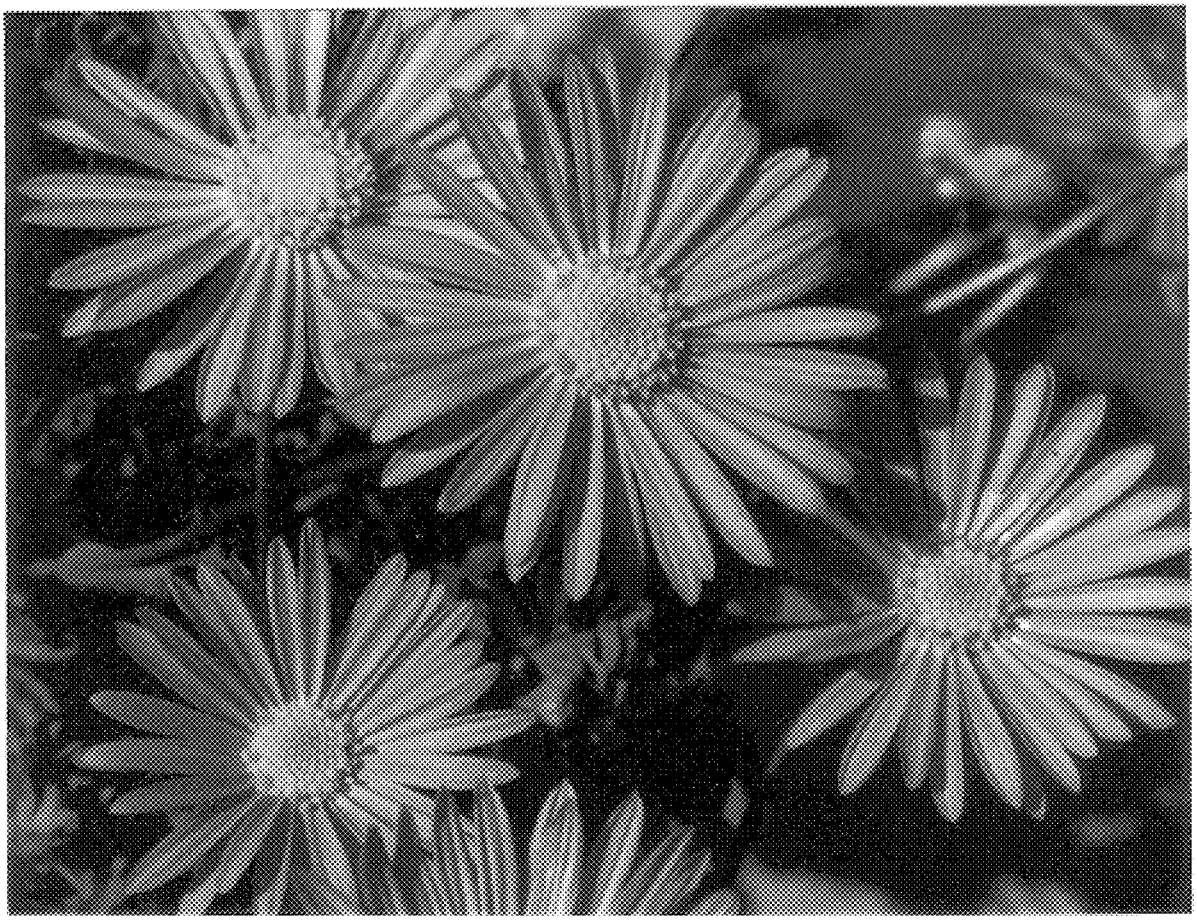

* * * * *